United States Patent [19]

Bezman

[11] 4,405,822

[45] Sep. 20, 1983

[54] DIISOPROPYL ETHER HYDRATION IN ISOPROPANOL PRODUCTION

[75] Inventor: Susan A. Bezman, Point Richmond, Calif.

[73] Assignee: Chevron Research Company, San Francisco, Calif.

[21] Appl. No.: 316,580

[22] Filed: Oct. 30, 1981

[51] Int. Cl.³ .............................................. C07C 29/04
[52] U.S. Cl. ..................................... 568/899; 568/907
[58] Field of Search .......................................... 568/899

[56] References Cited

U.S. PATENT DOCUMENTS

| | | | |
|---|---|---|---|
| 2,519,061 | 8/1950 | Mason | 568/907 |
| 2,648,711 | 8/1953 | Carrier | 568/899 |
| 2,813,908 | 11/1957 | Young | 568/899 |
| 2,818,439 | 12/1957 | Hakala et al. | 568/899 |

Primary Examiner—J. E. Evans
Attorney, Agent, or Firm—D. A. Newell; S. R. La Paglia; S. H. Roth

[57] ABSTRACT

A process for producing alcohols by the direct hydration of olefins in which the ether by-product is hydrated with a large molar excess of water in a reaction zone which precedes a propylene hydration reaction zone.

8 Claims, 1 Drawing Figure

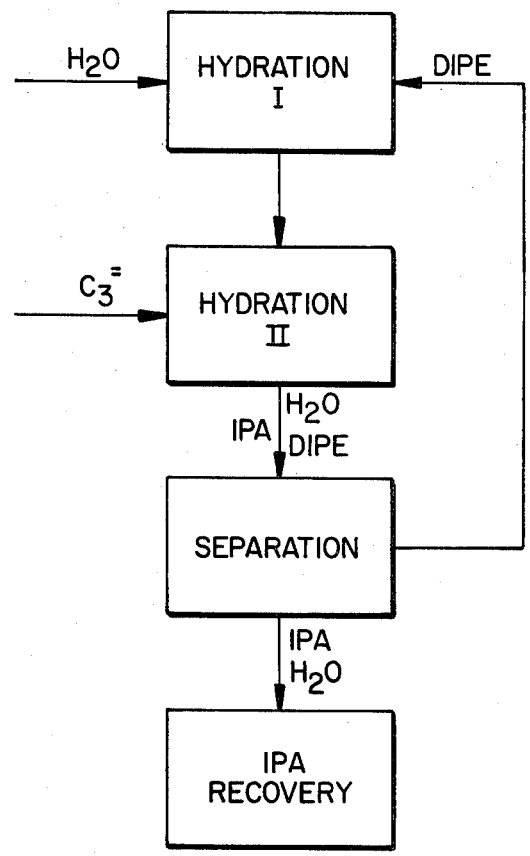

DIISOPROPYL ETHER HYDRATION IN ISOPROPANOL PRODUCTION

BACKGROUND OF THE INVENTION

The present invention relates to a process for the hydration of olefins. Specifically, the invention relates to a process for the hydration of propylene to produce isopropanol for blending into gasoline.

As is well known, alkylation can produce a premium grade gasoline component from olefins by reaction with isoparaffins such as isobutane or isopentane. Refineries have, however, experienced a shortage of isoparaffins, particularly isobutane, and therefore have an excess of olefins. So a way to place these olefins into the motor gasoline pool is needed. At the same time, gasoline octane requirements have increased and the use of traditional lead-containing gasoline additives has been largely discontinued. It has, therefore, become necessary to find alternative means to produce high octane fuel compositions without the necessity for alkylation. This may be accomplished by producing oxygenated compounds, e.g., isopropanol from the excess olefins.

Furthermore, some gasolines have a maldistribution of high octane components and when used without fuel injection can knock under driving conditions not predicted by model octane testing. Addition of isopropanol to such gasolines provides a good way to improve octane component distribution.

Isopropanol may be made with very high propylene conversions per pass using even dilute $C_3$ olefin-containing feedstocks at low space velocities and/or low water to olefin feed molar ratios. Under these conditions, however, large amounts of diisopropyl ether (DIPE) may be formed. The present process relates particularly to the treatment of the DIPE by-product so that the isopropanol production process can be conducted more efficiently. The present process is an improvement over that disclosed in my U.S. application entitled "Diisopropyl Ether Hydration in Isopropanol Production", filed concurrently herewith and incorporated by reference herein.

BRIEF DESCRIPTION OF THE DRAWING

The sole FIGURE is a flow diagram of a process for producing isopropanol in accordance with the invention.

SUMMARY OF THE INVENTION

The present invention relates to a process for producing alcohols by the direct hydration of olefins comprising the steps of contacting a first reactant stream comprising water and a recycle stream in a first reaction zone with a first catalyst comprising an acid ion exchange resin under direct hydration conditions to produce a first product stream; contacting the first product stream and an olefin-containing feed wih a second catalyst comprising an acid ion exchange resin under direct hydration conditions in a second reaction zone to obtain a second product stream; separating the second product stream into a third stream comprising water and product alcohol and a recycle stream; and passing the recycle stream into the first reaction zone.

DESCRIPTION OF THE PREFERRED EMBODIMENTS

The process of the present invention enables one to use excess $C_3$ olefins and incorporate them as high octane components into the motor gasoline pool without alkylation. In addition, the present process provides a method for employing the by-product of the propylene hydration reaction whereby this by-product is in effect incorporated into the motor gasoline pool.

The present invention constitutes an improved method for treating an ether by-product of an olefin hydration reaction. The process of the invention is essentially a two-zone reaction scheme in which the by-product is made to contact a large molar excess of water to force the by-product hydration reaction toward completion and to avoid recycling of a stream which contains an equilibrium quantity of by-product.

The process of the invention is described with reference to the hydration of propylene to produce isopropanol (IPA), but it is applicable to olefin hydration processes in general.

The present invention is most advantageously employed in a process for producing isopropanol by the hydration of propylene. Although any such process may be employed, the preferred method is the one disclosed in my co-pending U.S. patent application, Ser. No. 277,438, filed June 25, 1981 which is incorporated by reference herein. In that method, a feedstock comprising $C_3$ hydrocarbons having a propylene content of from about 60% to about 85% is used. Preferred is a feed such as that which could be obtained by distilling off a $C_3$ cut from a fluid catalytic cracker. It is possible by using the combination of reaction conditions described below to obtain a high conversion per pass even employing such dilute feedstocks.

The feedstock containing propylene is reacted with water in the presence of an ion exchange catalyst. In the process of the present invention, the olefin-containing feedstock is introduced into a second reaction zone in which the main olefin hydration reaction occurs. By-product ether is contacted with water and catalyst in a first reaction zone as discussed hereinbelow. The second reaction zone hydration catalyst is preferably a sulfonated macroreticular copolymer of styrene and divinylbenzene in the acid form. Catalysts modified by chlorination to withstand higher temperatures, such as Amberlyst XN 1011 and Amerlite XE-372, manufactured by Rohm and Haas, are particularly preferred. Other catalysts suitable for the direct hydration of propylene and methods for their preparation are described in U.S. Pat. No. 2,813,908, incorporated by reference herein.

In propylene hydration, a propylene-containing feedstock is generally mixed with water in a ratio of water to propylene from about 5 to 15, preferably from about 8 to 12 and most preferably about 8. The mixture is then fed to a reactor, preferably in a downflow, trickle bed configuration, to contact the catalyst.

Hydration conditions generally include a pressure of from about 1,000 to 2,000, preferably 1,400 to 1,500 psig and a temperature of from about 275° to 375° F., preferably from about 290° to 355° F. The conditions are selected so that the propylene is in a super-critical gas phase and the water is primarily in the liquid phase. Finally, the propylene liquid hourly space velocity is from about 0.15 to about 1.5 per hour, preferably from about 0.4 to 0.5 per hour.

In the hydration stage, the percent propylene conversion should be maintained at a predetermined level, generally from about 50% to 90%, preferably about 67%. To do so, the temperature in the reactor can be raised incrementally to compensate for the loss of catalyst activity during the course of the reaction.

The crude product which emerges from the bottom of the reactor generally contains water, isopropanol, diisopropyl ether (a by-product), propylene, propane, any $C_4$ hydrocarbons present in the feed, traces of alcohols or ethers derived from reactions of $C_4$ hydrocarbons, and traces of $C_6$ hydrocarbons formed by the dimerization of propylene. This crude product may be passed through one or more conventional gas-liquid separators to separate the gases, i.e., propane, unreacted propylene and trace $C_4$ and lower hydrocarbons from the liquids, i.e., isopropanol, water and diisopropyl ether.

The separated gases, generally contain at least 30% unreacted $C_3$ olefins. Such olefins, of course, may be fed to a conventional alkylation plant where they are allowed to react with isoparaffins in the presence of a suitable catalyst such as HF or sulfuric acid. The resultant alkylation product, presumably a mixture of high-branched $C_7$ paraffins is a high octane product suitable for direct addition to the motor gasoline pool. As discussed, the desirability of alkylation is limited by the shortage and high expense of the requisite isobutane.

Propylene obtained from the overhead of the liquid-gas separator may be catalytically oligomerized to make olefinic gasoline, a high octane gasoline pool component as disclosed in my co-pending U.S. application Ser. No. 277,437, filed June 25, 1981. Such oligomerization obviates the need to alkylate excess olefins, significantly reducing the process cost.

The crude liquid product from hydration which contains water, isopropanol, diisopropyl ether and perhaps traces of $C_4$ olefin-derived ethers and/or alcohols and $C_6$ olefins is generally caustic neutralized or acid is removed by ion exchange. This product is passed through a first distillation column which is generally operated at near atmospheric pressure at a temperature so that the product taken overhead is primarily diisopropyl ether (actually the low-boiling azeotrope which also contains 4% isopropanol and 5% water, b.p. 62° C.). The bottoms from this first distillation column, containing primarily isopropanol and water, are passed through a second distillation column. The overhead from the first column, primarily diisopropyl ether, is treated in accordance with the present invention as discussed hereinbelow.

The second distillation column containing the isopropanol and water, is operated generally at or near atmospheric pressure and at a temperature such that the isopropanol-water azeotrope (b.p. 80° C.) having the composition of 87.8 weight percent isopropanol and 12.2 weight percent water is taken overhead. The column bottoms which consist primarily of a very dilute aqueous salt solution may be either (a) desalted by treatment with an ion exchange resin and the pure water recycled with makeup water to the hydration reactor or (b) discarded.

Isopropanol is typically separated from the isopropanol-water azeotrope so it can be blended with a gasoline blending hydrocarbon stream resulting in a oxygenated fuel-containing blending stock which can be used directly in the motor gasoline pool. Such separation may be accomplished by any of the conventional extraction and/or azeotropic distillation techniques. The preferred method which provides a simple, economical way to introduce isopropanol from an isopropanol-water azeotrope directly into a gasoline blending stock, an extractive blending technique, is the subject of my co-pending U.S. patent application Ser. Nos. 277,295, 277,296 and 277,440, all filed June 25, 1981, and which are incorporated by reference herein.

Briefly, in accordance wih those methods, the azeotrope is dehydrated by combining it with a gasoline blending hydrocarbon stream. The gasoline blending hydrocarbon may be any hydrocarbon that can be added to the motor gasoline pool, including straight run, alkylate, FCC gasoline, reformate, or their mixtures such as Chevron Unleaded Regular gasoline (ULR). The mixing may be done in a mixing tank, but is preferably accomplished by use of inline mixers such as the pipe mixers manufactured by Komax Systems, Inc., as opposed to the energy intensive extractors. From about 2 to 15 volumes of hydrocarbon per volume of azeotrope, preferably at least 10 volumes are employed. A milky emulsion forms on mixing. This emulsion is separated rapidly into two phases for example by passing it through a commercial water filter coalescer.

For a 10:1 volume ratio, regardless of the rate of separation, the hydrocarbon layer composition is about 91.2 weight percent gasoline, 8.3 weight percent isopropanol and 0.41 weight percent water. The aqueous phase consists essentially of about 75% water and 25% isopropanol. This layer represents only a small volume of material, however, (less than 0.1) and may be recycled to the second distillation column. The isopropanol-hydrocarbon phase emerging from the coalescer can be blended with additional gasoline or used directly as automotive fuel without further treatment.

In accordance with the method disclosed in my application entitled "Diisopropyl Ether Hydration in Isopropanol Production", filed concurrently herewith, the effluent from a propylene hydration reaction is divided into a stream comprising water and isopropanol and another stream comprising the by-product diisopropyl ether which also generally contains about 4% isopropanol. This DIPE-containing stream is recycled directly to the hydration reaction zone.

In accordance with the present invention, the diisopropyl ether (ether by-product) is recycled to a first reaction zone containing a first hydration catalyst into which all of the water used for the second zone propylene hydration is fed thereby producing a very large molar ratio of water to DIPE to drive the DIPE hydration reaction closer to completion. The molar ratio of water to DIPE in the first reaction zone should generally be from about 20 to 600, preferably from about 40 to 250. This very large molar excess of water avoids the necessity of recycling an equilibrium quantity of DIPE and increases the amount of IPA produced.

The hydration catalyst in the first reaction zone may comprise almost any acid catalyst. For example, the first zone hydration catalyst may comprise ZSM-5 type zeolites, preferably the essentially alumina-free intermediate pore size zeolites such as silicalite as disclosed in U.S. Pat. No. 4,061,724, incorporated by reference. Silica-alumina cogels, alumina or acid ion exchange resins which are suitable for the propylene hydration reaction may also be employed.

The feed containing propylene is made to contact the effluent from this first reaction zone in a second reaction zone with a second hydration catalyst comprising an acid ion exchange resin under hydration conditions as discussed above. This second reaction zone may be contained in the same reactor as the first reaction zone or may be a separate reactor. Further, the catalyst in the first reaction zone may be the same or different from the catalyst in the second reaction zone. This may be accomplished by having different reactors or a layered bed of catalyst in a single reactor.

When the two reaction zones are maintained in the same reactor, the process may be conducted with a single catalyst, preferably Amberlite XE-372.

For such a configuration, hydration conditions include a temperature of from about 275°–375° F. and a pressure of from about 1000 to 2000 psi. The DIPE recycle stream has an LHSV of from about 0.03 to 1.0 hr.$^{-1}$ in the first reaction zone. The LHSV of the total hydrocarbon stream, i.e., the propylene-containing feedstock plus the organic effluent from the first reaction zone, is from about 0.15 to 1.5 hr.$^{-1}$.

When two catalyst beds are employed in a single reactor, hydration conditions in the first reaction zone will include a temperature of from about 300° to 500° F., a pressure of from about 1000 to 2000 psi and an LHSV or recycle DIPE of from about 0.03 to 1.0 hr.$^{-1}$. Hydration conditions in the second reaction zone will include a temperature of from about 275°–375° F., a pressure of from about 1000 to 2000 psi, and an LHSV of the total hydrocarbon stream of from about 0.15 to 1.5 hr.$^{-1}$.

The sole FIGURE is a flow diagram of a process for producing isopropanol comprising:

(a) contacting a reactant stream comprising water and diisopropyl ether in a first reaction zone (HYDRATION I) with a first hydration catalyst under hydration conditions;

(b) contacting the effluent from the first reaction zone and a feedstock comprising propylene with a second hydration catalyst comprising an acid ion exchange resin under hydration conditions in a second reaction zone (HYDRATION II);

(c) separating the effluent from the second reaction zone into a product stream comprising water and isopropanol and a recycle stream comprising diisopropyl ether (SEPARATION);

(d) passing the recycle stream to step (a) (HYDRATION I); and (e) recovering isopropanol from the product stream (IPA RECOVERY).

The following example is merely illustrative and is not intended to constitute a limitation on the invention which is defined by the appended claims.

EXAMPLE

Water and DIPE were fed in a 24:1 molar ratio over a bed of Amberlite XE-372 catalyst at 300° F. and 1440 psig. The product distribution was studied as a function of LHSV. Since "propylene" can be in any of three chemical forms in this system, i.e., $C_3^=$ IPA, DIPE, the product composition was expressed in terms of the molefraction of total available $C_3^=$ present in each form. Equilibrium was achieved at a DIPE LHSV of about 0.04–0.05 hr$^{-1}$. The equilibrium composition corresponds to 6% of the total $C_3^=$ in the form of propylene, 22% in the form of DIPE and 72% in the form of IPA. These results favorably correspond with the equilibrium data obtained by plotting product composition as a function of $C_3^=$ LHSV for the forward reaction, propylene hydration at a 12:1 water to propylene molar ratio by extrapolation to 0 LHSV.

Since equilibrium product compositions were achieved by either the forward or reverse reactions over Amberlite XE-372, DIPE recycle is clearly a viable processing option in a situation in which the by-product DIPE formation need not be kept very low. Such situations arise in which the molar ratio of water to propylene is less than about 12.

Although the present invention has been illustrated by reference to specific embodiments, it will be apparent to those skilled in the art that various changes and modifications may be made which clearly fall within the scope of this invention. It is not the intent of applicant to be bound by the specific embodiments described, but rather only by the appended claims.

I claim:

1. A process for producing isopropanol comprising:
   (a) contacting a reactant stream comprising water and diisopropyl ether in a first reaction zone with a first hydration catalyst under hydration conditions including a molar ratio of water to diisopropyl ether of from about 20 to 600;
   (b) contacting the effluent from the first reaction zone and a feedstock comprising propylene with a second hydration catalyst comprising an acid ion exchange resin under mixed phase hydration conditions in a second reaction zone including a temperature of from about 275° to 375° C. and a pressure of from about 1000 to 2000 psig;
   (c) separating the liquid effluent from the second reaction zone into a product stream comprising water and isopropanol and a recycle stream comprising diisopropyl ether;
   (d) passing the recycle stream to step (a); and
   (e) recovering isopropanol from the product stream.

2. The process of claim 1, wherein the molar ratio of water to ether contained in the recycle stream is from about 40 to 250.

3. The process of claim 1, wherein the second hydration catalyst is a sulfonated macroreticular copolymer of styrene and divinylbenzene.

4. The process of claim 3, wherein the second hydration catalyst is in a chlorinated form.

5. The process of claim 1, wherein the olefin-containing feed comprises $C_3$ hydrocarbons of which from about 60 to 85% are propylene.

6. The process of claim 1, wherein the first hydration catalyst is selected from the group consisting of intermediate pore size zeolites, alumina, silica-alumina and acid ion exchange resins.

7. The process of claim 1, wherein the molar ratio of water to diisopropyl ether in the first reaction zone is from about 20 to 600.

8. The process of claim 1, wherein hydration conditions in the first reaction zone include a temperature of from about 275° to 375° F., a pressure of from about 1000 to 2000 psi and a recycle stream LHSV of from about 0.03 to 1.0 hr.$^{-1}$.

* * * * *